US005888734A

United States Patent [19]
Cremer et al.

[11] Patent Number: 5,888,734
[45] Date of Patent: Mar. 30, 1999

[54] METHOD FOR PREPARING AND HYBRIDIZING SPECIFIC PROBES

[76] Inventors: Christoph Cremer, Mombertplatz 23, D-69126 Heidelberg; Dino Celeda, Burgunderstrasse 36, 67435 Neustadt; Ulrich Bettag, Oggersheimer Strasse 67, D-67227 Frankenthal, all of Germany

[21] Appl. No.: 746,305

[22] PCT Filed: May 19, 1993

[86] PCT No.: PCT/DE93/00460

§ 371 Date: Apr. 17, 1995

§ 102(e) Date: Apr. 17, 1995

[87] PCT Pub. No.: WO93/24652

PCT Pub. Date: Dec. 9, 1993

Related U.S. Application Data

[63] Continuation of Ser. No. 338,561, Apr. 17, 1995, abandoned.

[30] Foreign Application Priority Data

May 22, 1992 [DE] Germany .................. 42 16 949.6

[51] Int. Cl.⁶ ............... C12Q 1/68; C07H 21/02; C07H 21/04; C12N 15/00
[52] U.S. Cl. ............ 435/6; 536/23.1; 536/24.3; 935/76; 935/77; 935/78
[58] Field of Search .................. 435/5, 6, 810; 536/24.3; 935/76, 77, 78

[56] References Cited

U.S. PATENT DOCUMENTS

| | | | |
|---|---|---|---|
| 4,599,303 | 7/1986 | Yabusaki | 435/6 |
| 4,623,627 | 11/1986 | Huang et al. | 435/240 |
| 4,886,741 | 12/1989 | Schwartz | 435/5 |
| 4,888,278 | 12/1989 | Singer et al. | 435/6 |
| 5,223,414 | 6/1993 | Zarling et al. | 435/91 |
| 5,225,326 | 7/1993 | Bresser et al. | 435/6 |
| 5,273,881 | 12/1993 | Sena et al. | 435/6 |
| 5,436,144 | 7/1995 | Stewart et al. | 435/91.2 |
| 5,447,841 | 9/1995 | Gray et al. | 435/6 |
| 5,506,098 | 4/1996 | Zarling et al. | 435/6 |
| 5,589,333 | 12/1996 | Bagasra et al. | 435/6 |

FOREIGN PATENT DOCUMENTS

| | | |
|---|---|---|
| 0135159 | 3/1985 | European Pat. Off. . |
| 0336412 | 10/1989 | European Pat. Off. . |
| 0450370 | 10/1991 | European Pat. Off. . |
| WO 93/05177 | 3/1993 | WIPO . |

OTHER PUBLICATIONS

Durm et al., Zeitschrift fur Naturforschung, Section C, 52:82–88 (1997).
Durm et al., Brazilian J. of Medical Biological Research 30:15–23 (1997).
Haar et al., Biotechniques 17: 346–348 (1994).
"Use of Nucleotides as an Alternative to Formamide in Non–Radioactive in Situ Hybridization", Koji and Nakane, 1989.
"Colorimetric Detection of Herpes Simplex Virus by DNA in Situ Sandwich Hybridization . . . .", Iezzoni et al, 1992.
"Triple Helix Formation by Oligonucleotides on DNA Extended to the Physiological PH Range", Povsic et al, 1989.
"A Simplified Combination of DNA Probe Preparation and Fluorescence in–Situ Hybridization", Celeda et al, 1992.
PCR Amplification and Simultaneous Digoxigenin Incorporation of Long DNA Probes for Fluorescence in Situ Hybridization, Celeda et al, Biotechniques, vol. 12, No. 1, 1992.

*Primary Examiner*—W. Gary Jones
*Assistant Examiner*—Ethan Whisenant
*Attorney, Agent, or Firm*—Brinks Hofer Gilson & Lione

[57] ABSTRACT

A method of in situ hybridization (ISH) between nucleic acid or polyamide nucleic acid probes and chromosomal nucleic acid targets is taught, as well as, a kit for perform the method. In the inventive method the chromosomal nucleic acid targets are detected without any chemical or physical pretreatment of the chromosomal nucleic acid targets. In addition, the hybridization medium is to be substantially free of denaturants and the hybridization step is to be performed in the absence of catalytically effective amounts of enzymes.

19 Claims, No Drawings

METHOD FOR PREPARING AND HYBRIDIZING SPECIFIC PROBES

This is a continuation of application Ser. No. 08/338,561, filed Apr. 17, 1995 now abandoned, which was a 371 of international application No. PCT/DE93/00460.

The invention concerns a method for the in situ hybridization of specific probes, such as nucleic acids or polyamide nucleic acid probes suited for hybridization, to chromosomal targets containing nucleic acids. The method of in situ hybridization described herein involves bringing the nucleic acid or the polyamide nucleic acid probe into close spatial contact with the chromosomal target in an aqueous medium containing between 0% and 10% (v/v) denaturing substances. Targets with which the method can be utilized include eukaryotic chromosomes, particularly in mammalian cells and plant cells.

The analysis of chromosome structure has begun to play an important role in biological and medical research and diagnosis. For instance, in the study of pathological processes, a close correlation has been found between chromosome morphology and malignity. Several applications are known for in situ hybridization techniques, such as tumor research, detection of chromosomal mutagen-induced aberrations, and the study of the specific chromatin in the interphase nucleus.

In situ hybridization, i.e., the specific addition of specific probes, such as labelled nucleic acids and polyamide nucleic acids, to chromosomal targets is based on the hybridization of complementary strands. In situ hybridization of nucleic acid targets such as chromosomes and polyamide nucleic acid targets allows identification of the specific sequences present, as well as the location of these sequences on the chromosomes. If the probes are labelled, for instance with a fluorescent label, they can be detected and located after hybridization via this label.

Prior to the present invention, experts in this field believed that in situ hybridization (hereafter referred to as ISH) could only be successfully carried out when both the target and the probe deoxyribonucleic acid (DNA) were extensively present in singled-stranded form. This conviction has been clearly reflected in a variety of publications. These publications presuppose that natural, single-stranded sections, for instance due to replications contained in the DNA, would not be sufficient for ISH. It is generally presumed that a target-DNA is essentially present in double-stranded, i.e., duplex, form. Therefore, the double-stranded target DNA would need to be suitably treated prior to an ISH, in order to transform the target-DNA to a single-stranded form. For that reason, the known methods used for ISH are based on the use of formamide or other chemical agents which have a denaturing effect, to promote or maintain denaturation. Suitable enzymes, such as exonucleases, in combination with formamide at concentrations above 30%, may also be employed for producing single strands. A temperature increase of the medium containing the target is also considered beneficial for denaturation, however a temperature increase alone has not been considered sufficient.

Other solutions have consisted of the avoidance of thermal denaturation of the target-DNA. This is accomplished, e.g., by an appropriate quantitative increase in the use of agents having a denaturing effect, or which promote denaturation. Here, both agents are signified as denaturants. Hence, the target-DNA can be converted to a single-stranded denatured form at low temperatures, for example with NaOH or through the use of very high concentrations of formamide. Sensitive cell components, such as proteins are not sufficiently stable to such treatment. The option of using enzymes, such as exonucleases, is an alternative for the production of single-stranded target-DNA. In such enzymatic methods, however, the hybridization was performed with a buffer system containing formamide, albeit at a somewhat lower concentration than was deemed necessary in producing nonenzymatic, single-stranded target-DNA at low temperatures. As yet the possibility of a method for nonenzymatic ISH without the use of denaturants had not previously been derived.

The existing belief in the art that denaturants are absolutely necessary for a successful ISH has been so prevailing that even authors who conducted an ISH at low temperatures after enzymatic treatment thereafter used additional denaturants, which denaturant in the specific case was formamide. The notion that the double-stranded DNA would prior to hybridization need to be converted to single-stranded target-DNA by appropriate treatment was so firmly accepted that no control experiments were conducted that did not include treatment with formamide.

The use of formamide drastically lowers the melting temperature of double-stranded DNA (ds-DNA). Furthermore, on the basis of energetic considerations, it may be expected that the formation of triplex DNA might, in the presence of formamide, possibly be disturbed even more strongly than the formation of ds-DNA.

Chromosomal proteins are of considerable significance for the tertiary structure of chromosomes, including chromosomal DNA. Therefore, alterations of the tertiary structure of chromosomal proteins could considerably influence the conformation of the chromosomal DNA, for instance the creation of triple formations. Since the tertiary structure of proteins can be greatly disturbed by denaturants, formamide and other denaturants might also in this respect have an influence which ultimately impedes the ISH. Considerations similar to that for formamide also apply to other denaturants. For clarity, the term "denaturant" or "denaturing substance" shall be referred to as a substance which lowers significantly the melting temperature $T_m$ of deoxyribonucleic acid in solution at given conditions of pH, temperature, and ionic strength. The term "significantly" is intended to denote a lowering of $T_m$ by at least 5° C.

The known ISH methods have considerable disadvantages in application. For example, denaturing substances such as formamide do not selectively exert their denaturing effect on nucleic acids. The denaturing effect may also be exerted on other cell components, such as proteins. Therefore, immunotechnical staining methods (IT) perform only in a limited manner in the presence of such denaturants, due to their effect on other immunologically relevant structures. For this reason it is generally not possible, or is possible only at great expense, to combine ISH methods with immunological staining methods, even though such a combination would be very desirable in order to obtain rapid and reliable diagnoses, particularly in the field of clinical diagnostics. All of the known processes seeking to combine IT and ISH, however, are restricted to relatively rare, naturally occurring immunologically relevant structures, which structures are sufficiently resistant to thermal denaturation and/or treatment with denaturants, or alternatively, to the preparation and use of resistant immunological structures. If ISH and IT are to be combined in a method, an IT reaction with antibodies that have been biotinylated, or with other thermally and otherwise resistant groups, would be performed first, and only thereafter would the ISH procedure be performed. However, this combined method is relatively time-consuming and expensive.

A general method to utilize the simultaneous characterization of cells by immunological techniques (IT) and ISH methods with chromosomal targets has not been available for use with the present ISH methods, since the preparatory steps involved in the method impair the immunological staining to a considerable degree.

The problem underlying the present invention is to provide an ISH method that may be performed simpler, faster and more economically than conventional methods, and in which the targets, for instance chromosomes, cells or tissues, undergo a more sparing treatment, thereby making possible the combination of the ISH method with immunological techniques.

This problem is solved by the method of the present invention, wherein (a) the chromosomal targets, without any chemical or physical denaturing pretreatment, (b) a hybridization reagent, comprising the probes in a medium, and (c) an aqueous buffer medium, are mixed together, thereby bringing the targets and probes into close spatial contact for initiating and performing the hybridization under non-denaturing conditions.

The inventional method provides a considerable simplification and reduction of procedural steps, when compared to known methods. In the inventive method, denaturants are omitted completely, or alternatively, they are utilized only in relatively small amounts not greater than 10% (v/v), at which concentration the denaturants do not have a negative effect on even sensitive structures. A more sparing treatment of targets is thereby obtained, and expensive procedural and washing steps linked to the use of higher denaturant concentrations may be omitted.

As a result of the reduction of process steps and of the time required for use of the inventive process, a good morphology of the chromosomal material and a good visualization of the labelled probes may be obtained. Furthermore, a better and more rapid detection by means of quantitative methods of image analysis may also be obtained. More specifically, a reduced statistical fluctuation of intracellular hybridization signal conditions is achieved, with the inventional method being performable within a very short time of less than 30 minutes, and in many cases, less than five minutes. Owing to its simplicity and rapidity, the inventive method also is suited for examination, or evaluation, of larger amounts of material in a very short time. Statistical methods of examination, in particular, may be optimally utilized, such as when detecting radiation-induced, or chemically induced, chromosome alterations in the low-dose range. The effect of low doses of radiation can thus be detected on the chromosomes in an appreciably simpler and faster way, so that it is possible to determine rates of aberration, or chromosomal alterations.

One particular advantage of the invention is that in performing the ISH it is possible to completely omit denaturants, such as formamide, and also omit enzymatic treatment, and that the chromosomal targets need not be subjected to temperatures above 45° C. Denaturants and enzymatic treatments for the production of single-stranded DNA sections are thus no longer required.

The inventional method also results in labellings that are characteristic for specific ISH, even though during the entire ISH procedure the target was not treated with denaturants. The addition of small amounts of denaturants has in many cases no negative effect, provided that the denaturant concentration remains below 10%.

The present invention shows that the prevailing belief that has existed for decades, namely that a successful ISH can work only when using denaturants in elevated concentrations, meaning in practice at concentrations above 30%, and with appropriate physical measures or appropriate enzymes, such as exonucleases, is surprisingly not correct. Contrary to the prevailing beliefs, sufficient targets for reliable hybridization of the probes to specific positions of these targets to specific positions of these targets may be single- or double-stranded in the novel ISH method.

Temperature plays an important role in a successful ISH. The optimal temperature of the hybridization mixture (i.e., the aqueous medium containing at least the probes and the targets) depends on the objective associated with the ISH. Generally, the novel ISH method can be performed at any temperature between −20° C. and 100° C. When combining the ISH with IT, it is preferred that the hybridization mixture is treated at relatively low temperatures between −20° C. and 45° C., more preferably between 2° C. and 37° C., and most preferably between 18° C. and 28° C. Thus, the ISH can also be performed at room temperature. As a result, thermal denaturation of the target can be omitted, and yet the very sensitive immunologically relevant structures remain unaffected. In such combination of ISH and IT, the ISH is commenced by addition of the probe, which was previously subjected to thermal treatment.

By suitable adjustment of the hybridization temperature, it is also possible to stringently control and prevent binding of the probe to chromosomal targets having low complementarity to the probe.

The simultaneous evaluation of sample preparations according to in situ hybridization parameters and immunological parameters, such as surface antigens, has great significance in clinical diagnostics. As a further development of the invention, specimen analysis may occur simultaneously by surface antigens and chromosome alterations with selective length of the labelled target sequence by microscopic observation, and/or digital microscopy, and/or flow cytometry techniques and like techniques, in such a way that the cell remains extensively undamaged, and that the targets can at the same time be made identifiable. This allows a classification of the individual targets in a very short time.

For a simultaneous immunological staining and low-temperature ISH (hybridization temperature<45° C.) a method is used which allows a sufficient permeability of the cell membrane without causing its destruction and without decisively altering the antigen expression of the cell surface. For this purpose, detergents may optionally be contained in the medium.

In the inventional low-temperature ISH, the chromosomes are treated using existing fixing methods (methanol/glacial acetic acid; glutaraldehyde, formaldehyde etc.). However, these are not denaturants, and they are not required for the hybridization process as such. Alternatively, such fixing methods may be omitted altogether.

It is essential in the invention that the extraordinarily stable ds-DNA-PNA complexes also result in an effective ISH at low temperatures below 28° C., even with the number of bases of the PNA sequences that lead to usable ds-DNA-PNA complexes remaining relatively small.

Dependent upon the circumstances, it is possible to perform the ISH method with single-stranded or double-stranded probes, although single-stranded probes are preferred. When probes are available initially in double-stranded form, these probes may be denatured by heating to temperatures above 50° C., preferably between 90° C. and 100° C. The renaturation time can be greatly extended by quick cooling to a temperature below 45° C., preferably below 10° C., so that the probes may be stored for a certain time in single-stranded form, prior to their addition to the hybridization mixture. The optimum denaturation temperature for double-stranded probes, among others, depends on the type of medium in which the probes are contained. In physiological common salt solution, for example, the optimum temperature ranges between 94° C. and 98° C.

In certain cases, for instance in the hybridization of single-copy sequences, the entire hybridization mixture including targets and probes is preferably heated to a temperature between 50° C.and 100° C., more preferably between 70° C. and 98° C., and most preferably between 80° C. and 98° C. The ISH proper then takes places during and/or after completed cooling to temperatures between −20° C. and 45° C., preferably between 2° C. and 37° C., and most preferably between 18° C. and 28° C. When examining repetitive sequences (for instance, from satellite II/III), which in practice is primarily the case, the duration of the hybridization phase ranges preferably between 15 seconds and 5 minutes, specifically between 20 seconds and 1 minute. When examining such single-copy sequences, the duration of the hybridization phase may take up to three days, in order to obtain expressive labellings.

It is particularly significant for the present invention that the integrity and even the viability of target cells is not decisively impaired by conducting the method at low temperature. For better binding to double-stranded native, specific sequence sections of the target-DNA, probes with suitably modified or substituted sugar-phosphate backbone may also be used. Sequence here refers to a molecule with a specific succession of the bases, whether native or synthetic, with normal, modified or substituted sugar-phosphate backbone. The natural sugar-phosphate backbone of nucleic acids can be substituted, e.g., by a polyamide chain. The polyamide nucleic acids (PNA) that are obtained hybridize better with targets than conventional nucleic acids, due to their specific physical properties.

Irrespective of the nature of the probe used, the probe is preferably labelled in some manner to enable its detection, or location, upon completed hybridization. A fluorescent label, such as FITC. (fluorescein-iso-thio-cyanate), is preferred, however other labelling methods may be used as well, such as biotin labelling or radioactive labelling. Different probes with different labellings may also be used.

The aqueous medium in which the ISH is carried out is preferably a physiological common salt solution. The medium may additionally contain buffer substances, such as tris-HCl, HEPES or potassium hydrogen phosphate with a pH between 5.0 and 8.7.

It is also favorable if the medium contains between 1 and 50 mmol/l, preferably 3 mmol/l of $MgCl_2$, as well as, optionally, gelatin or other substances for increasing the viscosity of the medium, since this will facilitate an amplification of the probes if desired. The medium for the ISH may also contain detergents if desired.

Performed preferably by means of polymerase chain reaction (PCR), the amplification of the probes may take place in a separate operation or in an aqueous medium in which the ISH takes place. The labelling of the probe may be carried out simultaneously with its amplification.

The inventional method allows a considerable extension and simplification of the chromosome diagnostic options in dividing cells, and also in nondividing cells. The new method allows the simplified selective labelling of whole chromosomes, chromosome sections and genes down to a length of a few hundred base pairs.

An important application of the inventive ISH method is in clinical tumor diagnostic applications, including therapy planning, prognostics and therapy control. It is expected that the ISH method will meet with broad acceptance, and will develop into a standard method of clinical laboratory diagnostics.

The following is a brief summary of the important advantages of the novel ISH method without addition of denaturants to the hybridization mixture:

Simplification of the entire ISH method by elimination of previously necessary procedural steps, such as washing steps;

Shortening of the entire ISH method, thereby obtaining reliable results after only a few minutes in some instances;

More sparing treatment of the examined material, so that the morphological integrity of the material may be better upheld;

Possibility of simultaneous performance of ISH methods and other test procedures, for instance with immunological techniques, in the same medium.

The method described hereafter allows the performance of ISH of specific probes, notably nucleic acid or DNA probes or other probes suited for hybridization, which possess a specific sequence of nucleotides, the probes being labelled with modified nucleotides and hybridized by ISH to specific positions of the targets. One or more labelled probes, also with several different labellings, may be brought in contact with the examined chromosomal target in a suitable aqueous medium, such as a buffer fluid with a pH between 5.0 and 8.7, or also in a physiological common salt solution at a temperature between −20° C. and 45° C. (low-temperature hybridization), after previously heating the hybridization mixture to temperatures between 50° C. and 100° C. (high-temperature hybridization). As a result, the probes undergo a specific hybridization with complementary sequences of the target. Unhybridized sequences are subsequently removed by washing. The probes hybridized to the target are then detected and/or located by a suitable method, such as fluorescence microscopy and/or flow cytometry. During the entire method there are either no denaturants present, or if present, present only in concentrations below 10% in the hybridization mixture.

The following is a detailed explanation of the novel ISH method using repetitive DNA samples (from satellite II/III), with the aid of modifications both for high-temperature and low-temperature ISH.

High-Temperature ISH

EXAMPLE I:

Chemicals used:

| | |
|---|---|
| Labelled DNA probes (immunofluorescence labelled) | 1–70 ng |
| Hybridization buffer 10x: (tris-HCl: 1–200 mmol/l; $MgCl_2$: 1–50 mmol/l; KCl: 1–600 mmol/l; gelatin: 1–10 mg/l) | 3 µl |
| Sodium citrate, saturated, 20x: | 3 µl |
| $H_2O$ to obtain final volume of | 30 µl |

Final volumes (30 µl) are applied on slides with fixed metaphase chromosomes (target-DNA) and hermetically sealed. The probe-DNA and target-DNA are incubated at 95° C. for 5 minutes, followed by incubation at 40° C. for 30 minutes. Next, the slides are washed 1x in the physiological common salt solution, Tween 20 (0.2% vol/vol) for 5 minutes at room temperature. Thereafter the slides are air dried, antibody conjugate is applied, followed by dissolution in the physiological common salt solution, Tween 20 (0.2% vol/vol). The slides are sealed airtight and incubated at room temperature in the dark. With "direct fluorescence," the antibody binding is eliminated after washing in the physiological common salt solution, Tween 20 (0.2% vol/vol). The slides are now in condition for analysis.

EXAMPLE II:

Chemicals used:

| | |
|---|---|
| Labelled DNA probes (immunofluorescence labelled) | 1–70 ng |
| Physiological common salt solution to obtain final volume of | 30 µl |

The method is performed as described in Example I.

Low-Temperature ISH

EXAMPLE III:

Chemicals used:

| | |
|---|---|
| Labelled DNA probes (immunofluorescence labelled) | 1–70 ng |
| Physiological common salt solution to obtain final volume of | 30 µl |

Prior to application on the slides with the fixed chromosomes (target-DNA), the probes are subjected to a thermal treatment of 5 minutes duration at 95° C. in the physiological common salt solution and then cooled immediately to −20° C. The probes are then applied at room temperature (20° C.) on the slides with the fixed chromosomes (target-DNA), sealed airtight and incubated for 10 hours at 37° C. For further steps for immunofluorescence and direct fluorescence, refer to Examples I and II.

These protocols were successfully used also for alphoid sample-DNA (D15Z1).

In practice, appropriate test kits can be offered for performing the novel ISH method. Such test kits consist preferably of at least one aqueous medium and of probes, preferably amplified probes, and/or labelled or other synthetically made probes. A washing solution may be provided for the test kit, preferably one not containing any denaturants. The probes are labelled, specifically by incorporation of modified nucleotides for direct or indirect immunofluorescence or radioactive groups, by coupling to a suitable fluorochrome or by other methods common in biochemistry. It is important for this labelling that the specifically bound probes can be detected and located after completed ISH. In a preferred embodiment, the test kit also contains one or more reaction vessels.

As stated above, the inventional ISH method is suited for combination with immunological staining methods, with both methods able to be performed simultaneously, and in the same medium. An appropriate test kit for such use contains in addition to the components utilized for the ISH method, such as probes and buffers, washing solutions and reaction vessels, at least one antibody directed specifically against cellular antigens and appropriately labelled. Furthermore, such test kit may also contain a secondary labelled antibody directed against primary antibodies. The aqueous medium containing the various components is preferably a physiological common salt solution or a buffer such as may be used also for the polymerase chain reaction (PCR), and optionally, saturated sodium citrate.

When the probes for the ISH are offered in single-stranded form, they may be stored together with the primary antibodies for the immunological test. In this case, the entire test kit could be comprised of a single vessel containing:

Aqueous medium, for instance physiological common salt solution,

Probes,

Antibodies.

An example of a test kit for the novel ISH is described hereafter. This test kit consists of four vessels. Vessels 2 and 3 contain buffer, vessel 1 contains the probe-DNA, and vessel 4 contains the physiological common salt solution.

Vessel No. 1 contains a selective amount of prelabelled (for instance labelled by direct fluorescence) probes in $H_2O$.

Vessel No. 2 contains hybridization buffer:

| | |
|---|---|
| Tris-HCl | 1–200 mmol/l |
| $MgCl_2$ | 1–50 mmol/l |
| KCl | 1–600 mmol/l |
| Gelatin | 1–10 mg/l |

Instead of KCl and gelatin, vessel No. 3 contains: polyoxyethylene sorbitan monooleate (Tween 20) 0.1–50 mg/l, and octyl phenol ethylene oxide condensate 0.1–50 mg/l.

Instead of the hybridization buffer according to the content in vessel No. 2 or 3, a physiological common salt solution may be utilized. Preferably, a saturated sodium citrate is also used in the buffer (vessel 2, 3).

Vessel 4 contains in the physiological common salt solution (Tween 20), an antibody labelled for immunofluorescence.

As stated, the kit consists of the four vessels No. 1 through 4. For the washing step after hybridization, a physiological common salt solution (0.9% vol. NaCl) must also be prepared by the user. This washing solution may additionally contain 0.2% vol. of polyoxyethylene sorbitan monooleate.

The antibody binding with indirect immunofluorescence is carried out in physiological common salt solution, with or without polyoxyethylene sorbitan monooleate (Tween 20). The washing step(s) after antibody binding take(s) place in physiological common salt solution.

We claim:

1. A method for performing in situ hybridization between nucleic acid or polyamide nucleic acid probes suited for in situ hybridization and chromosomal targets containing nucleic acids, the method comprising:

providing (a) the chromosomal targets, without any chemical or physical denaturing pretreatment, (b) a hybridization reagent, said hybridization reagent comprising the probes in a medium; and (c) an aqueous buffer medium;

combining said components (a), (b) and (c) to form a mixture, thereby bringing said targets and said probes into close spatial contact for initiating and continuing the hybridization, said mixture being substantailly free of denaturants; and performing said hybridization in the absence of catalytically effective amounts of enzymes.

2. The method of claim 1, wherein the mixture of the components (a), (b), and (c) contains denaturing substances in a concentration of 0% (v/v).

3. The method of claim 1, wherein the in situ hybridization between probes and targets takes place at a temperature between −20° C. and 45° C.

4. The method of claim 1, wherein the in situ hybridization between probes and targets takes place at a temperature between 2° C. and 37° C.

5. The method of claim 1, wherein the in situ hybridization between probes and targets takes place at a temperature between 18° C. and 28° C.

6. The method of claim 1, wherein the mixture of components (a), (b) and (c) is heated to a temperature between 50° C. and 100° C., and subsequently cooled in an actively controlled manner to a temperature between −20° C and 45° C.

7. The method of claim 6, wherein said mixture is heated to a temperature between 80° C. and 98° C. and cooled to a temperature between 18° C. and 28° C.

8. The method of claim 6, wherein said actively controlled cooling lasts between 15 seconds and 5 minutes.

9. The method of claim 1, wherein prior to the step of mixing components (a), (b) and (c), the probes are heated to a temperature between 50° C. and 100° C., and subsequently cooled in an actively controlled manner to a temperature between −20° C. and 45° C.

10. The method of claim 9, wherein said probes are heated to a temperature between 80° C. and 98° C. and cooled to a temperature between 18° C. and 28° C.

11. The method of claim 9, wherein said actively controlled cooling lasts between 15 seconds and 5 minutes.

12. The method of claim 1, wherein said aqueous medium comprises a physiological common salt solution, said physiological common salt solution comprising a solution of 0.9% sodium chloride in water.

13. The method of claim 1, wherein the aqueous medium comprises at least one of (a) $MgCl_2$, in an amount between 1 and 50 mmol/l $MgCl_2$; and (b) a buffer.

14. The method of claim 13, wherein the aqueous medium further comprises at least one of gelatin, polyoxyethylene sorbitan monooleate and octyl phenol ethylene oxide condensate.

15. The method of claim 1, wherein the aqueous medium further comprises at least one of sodium citrate and a detergent.

16. The method of claim 1, wherein the probes include a label selected from the group consisting of fluorochrome, biotins and radioactive labels.

17. The method of claim 1, wherein each of said probes includes a detectable label, and wherein said labels are detected after said hybridization by at least one of microscopic evaluation, digital microscopy and flow cytometry.

18. A test kit for performing in situ hybridization between nucleic acid or polyamide nucleic acid probes suited for in situ hybridization and chromosomal targets containing nucleic acids, in an aqueous medium comprising denaturing substances at a concentration between 0 and 10% (v/v), the test kit comprising the following components:

labeled nucleic acid probes or polyamide nucleic acid probes complementary to target DNA sequences;

a physiological common salt solution;

at least one labeled antibody capable of specifically binding to cellular antigens; and a buffer; wherein said components include denaturing substances in a concentration between 0 and 10% (v/v).

19. The test kit of claim 18, wherein said at least one labelled antibody comprises primary and secondary antibodies, said secondary antibodies specifically directed against said primary antibody; said buffer comprises at least one of tris-HCl; $MgCl_2$; KCl; and gelatin; and said physiological common salt solution comprises at least one member selected from the group consisting of polyoxyethylene sorbitan monooleate and 0.9% NaCl.

* * * * *